United States Patent [19]

Blaha et al.

[11] 4,175,826

[45] Nov. 27, 1979

[54] ADJUSTABLE VIEWING HEAD FOR A STEREOSCOPIC MICROSCOPE

[75] Inventors: Erich Blaha, Essingen; Kurt Schulz, Oberkochen, both of Fed. Rep. of Germany

[73] Assignee: Carl Zeiss-Stiftung, Oberkochen, Fed. Rep. of Germany

[21] Appl. No.: 855,673

[22] Filed: Nov. 29, 1977

[30] Foreign Application Priority Data

Dec. 3, 1976 [DE] Fed. Rep. of Germany ....... 2654778

[51] Int. Cl.² .............................................. G02B 21/22
[52] U.S. Cl. .......................................... 350/36; 350/75
[58] Field of Search ....................... 350/36, 35, 85, 23, 350/26, 75, 48–52

[56] References Cited

U.S. PATENT DOCUMENTS

| 2,132,122 | 10/1938 | Ott | 350/52 |
| 2,138,665 | 11/1938 | Ott | 350/85 |
| 2,439,526 | 4/1948 | Ott | 350/52 |
| 2,453,257 | 11/1948 | Ott | 350/85 |
| 3,040,626 | 6/1962 | Griffioen | 350/85 |

FOREIGN PATENT DOCUMENTS 713243  8/1954  United Kingdom ...................... 350/35

Primary Examiner—Jon W. Henry
Attorney, Agent, or Firm—Hopgood, Calimafde, Kalil, Blaustein & Lieberman

[57] ABSTRACT

The invention contemplates a viewing-head attachment removably securable to the body of a microscope and adapted to accommodate binocular viewing elements. The attachment employs two housings which are pivotally connected so that the binocular-viewing elements on one housing are enabled to stereoscopically view an object examinable under the microscope body to which the attachment is secured. The quality of stereoscopic viewing is unaffected regardless of the instantaneous pivot-angle relationship as between the two housings, and no further optical adjustments are needed.

2 Claims, 4 Drawing Figures

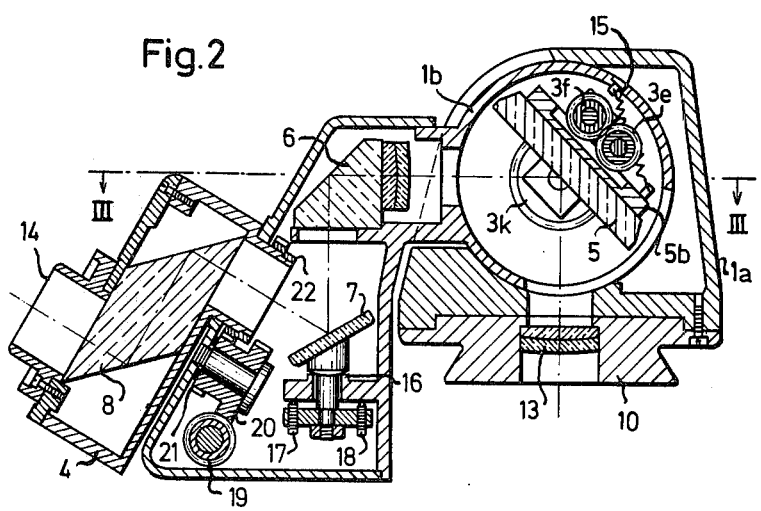
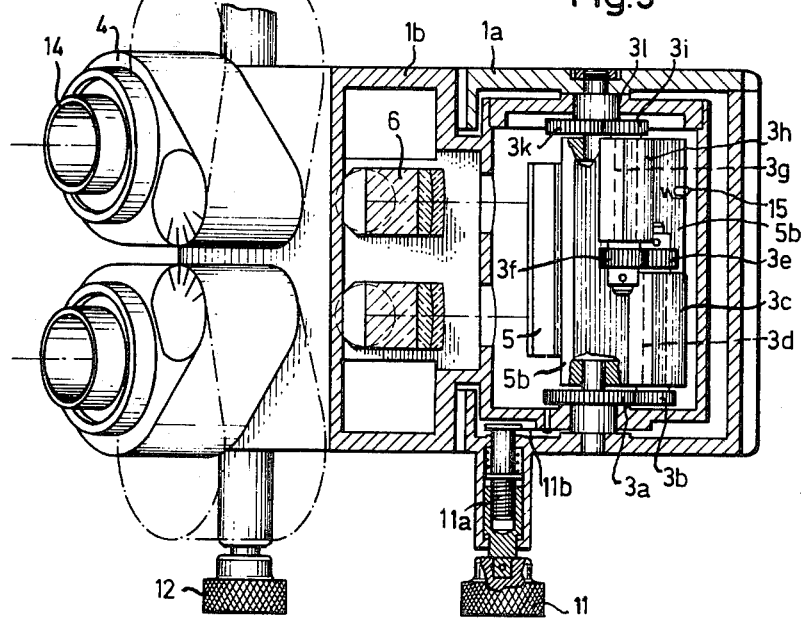

ADJUSTABLE VIEWING HEAD FOR A STEREOSCOPIC MICROSCOPE

The present invention relates to a stereoscopic microscope tube with optical beam take-up.

Stereoscopic microscope tubes with optical beam take-up are used mainly for operation microscopes in microsurgery. In this field, a minimum working distance between microscope eye lens and the object to be examined is desirable together with the required large objective focal length in order to permit the surgeon a relaxed posture in the performance of his work.

There are stereoscopic microscope tubes for surgical microscopes known in the art which by optical beam take-up shortens the working distance between the microscope eye lens and the object to be examined to the desired distance. These known microscope tubes are designed, however, only for a certain observation angle. These involve either straight tubes with observation direction in the direction of the optical axis of the microscope or parallel to this direction, or inclined tubes where the observation direction makes an angle of about 45° with the optical axis of the microscope. In related fields of technology, for example in precision mechanics, there are also known microscope tubes having a variable observation angle. However, these are not suited for the stereoscopic observation so important in microsurgery, because they are not accommodated for two laterally spaced stereoscopically related inlet-ray bundles.

It is an object of the present invention to provide a microscope tube which combines a continuous variation of the observation angle with short working distance and stereoscopic optical paths.

This object is achieved by the present invention as follows: The tube is made up of two interlocking housings, with the first housing being rigidly connected to the microscope body and the second housing being flexibly connected to the first.

In an expedient embodiment of the present invention, the first housing, connected rigidly to the microscope body contains an inlet objective and an optical deflection system coupled via a drive with the second, movable housing; eyepiece mountings for holding the eyepieces are movably mounted on the second, movable housing.

Preferably, the optical deflection system comprises a reflecting mirror coupled via the drive with the movable housing, and being of such effective area proportions as to accept incidence of both inlet-ray bundles and to reflect said bundles alike, a 45° roof prism, a rigid but adjustable reflecting mirror fastened in the second housing, and a rhomboid prism.

In a preferred embodiment of the present invention, the viewing mountings for holding the eyepieces can be turned by more than 90°.

An advantage, achieved by this invention, is that a surgeon is assured a relaxed and convenient posture while doing his work, and the change in viewing direction into the microscope, which is frequently desired during an operation, can be achieved by a single manual operation. This constitutes a considerable advance in the present state of the art, since previously changing the viewing angle of surgical microscopes could be achieved only by changing the tube of the microscope.

Other objects and various further features of novelty and invention will be pointed out or will occur to those skilled in the art from a reading of the following specification, in conjunction with the accompanying drawings. In said drawings, which show preferred and illustrative forms of the invention:

FIG. 2 shows a section taken through the microscope tube in accordance with the present invention in the inclined viewing position;

FIG. 3 shows a section taken along line III—III of FIG. 2; and

Figure 1:
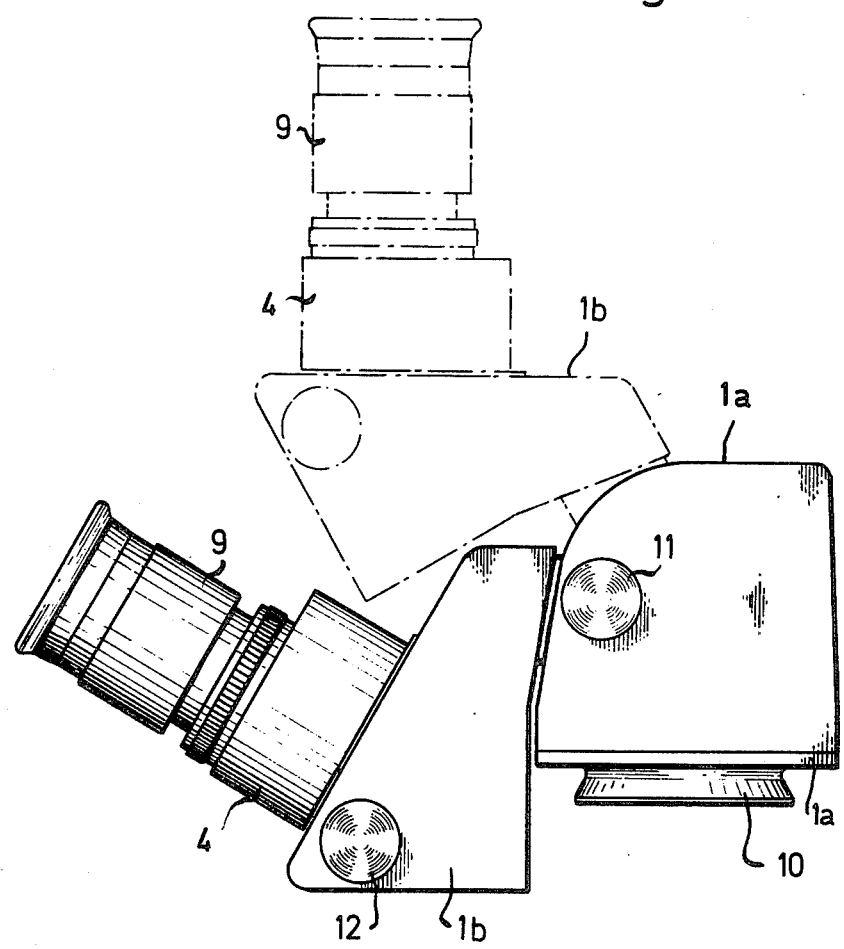
FIG. 1 shows a side view of the microscope tube in the positions "inclined viewing" and "straight viewing"

In the view of the microscope tube in accordance with the invention, shown in FIG. 1, the immovable housing part of the tube, which part is rigidly connected to the microscope body, is denoted by 1a. The connection to the microscope body is made via the ring mounting 10. The movable housing part is denoted by 1b and engages the rigid housing part 1a. In the view shown, the tube for inclined viewing is denoted by solid lines. The tube in the position for straight viewing is drawn by broken lines. The continuously variable pivot range is 60°. By means of the locking system 11, 11a, 11b, any angle position of housing 1b can be set between the two extreme viewing positions shown. The viewing mount 4, in which the eyepieces 9 are inserted, are pivotable for adjusting for eye distance and for adaptation to the chosen viewing direction. For example, the viewing mounts are pivoted from the position for inclined viewing by 90° to switch to straight viewing. The pivoting movement is started in the embodiment shown via the operating knob 12 and proceeds via a drive shown in FIG. 4.

In the section of FIG. 2, the optical deflection system used for beam take-up is shown. The mirror, coupled via the drive 3 to the movable tube housing 1b is denoted by 5, the 45° roof prism by 6; the reflecting mirror independent of the movement of drive 3 is denoted by 7, and the rhomboid prism used for parallel displacement of the image-forming beam is denoted by the numeral 8. The objective 13, via this deflecting system, reproduces the object in the intermediate image plane 14. There the image is viewed with the eyepiece 9. The mirror 5 must be dimensioned large enough so that it reflects both optical paths required for stereoscopic viewing. When changing the viewing direction, the locking screw 11 is loosened and the portion of housing 1b projecting downward in FIG. 2 is moved by hand. The cylindrical portion of housing 1b projecting into the housing portion 1a participates in the movement. Housing 1a is coupled to the mirror 5 via the planetary gear drive 3. The drive gear 3a, as shown in FIG. 3, is connected to housing 1b and mounted rotatably in housing 1a. It meshes with gear 3b which is mounted on a shaft 3d in bearing block 3c, and is fastened to holder 5b of mirror 5. At the other end of the shaft 3d, gear 3e is mounted and engages gear 3f. Gear 3f is fastened to shaft 3g and rotates in bearing 3h. The bearing 3h also is connected solidly to mirror holder 5b. On the other side of shaft 3g is gear 3i which meshes with gear 3k. The gear 3k in turn is rigidly connected to housing 1a, and its cylinder adjoint piece forms at 3-1 a pivot bearing for the housing 1b. The gears of planetary gear drive 3 are dimensioned so that when shifting the viewing direction by the angle α, the mirror is rotated by the angle α/2. The gear drive backlash resulting from manufacturing tolerances is compensated by a spring 15. The reflecting mirror 7, for the purpose of binocular adjustment, is accessible from the outside and mounted in a spherical segment 16, screws 17, 18 are used for adjustment. During locking of the movable housing 1b, by actuating rotary knob 11, screw 11a pushes a spring 11b against the housing wall 1a, causing a jamming effect. The broken-line position of the viewing mount 4 in FIG. 3 indicates the adjustability of the interocular distance by means of adjusting screw 12.

Figure 4:
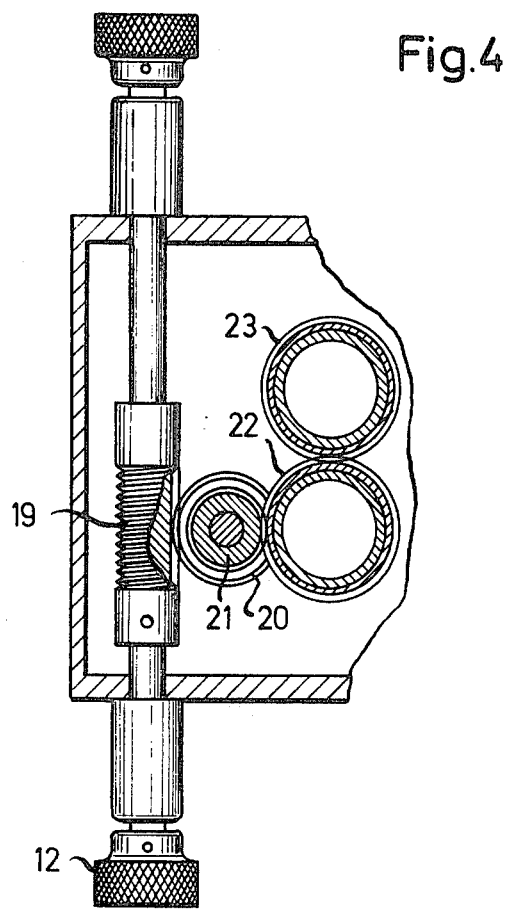
FIG. 4 shows a view of the drive for pivoting the viewing mount which is independent from the pivoting of the housing.

For the drive, shown in FIG. 4, for tilting the viewing mount, a worm operated by operating knob 12 is denoted by the numeral 19. This worm engages wormwheel 20, which in the upward continuation of its axis is a gear 21 and drives gear 22. Gear 22 in turn engages gear 23, moving the viewing mounts 4 connected to the gears 22 and 23. The above-described drive for moving the eyepiece mounts ensures adjustment to the interocular distance of the viewer and the adaptation of the eyepiece position for using the tube for inclined viewing and straight viewing.

What is claimed is:

1. As an article of manufacture, a binocular viewing head for a stereoscopic microscope, said head comprising a first housing having a ray-inlet side adapted to be mounted to a microscope body and adapted to accommodate two laterally spaced stereoscopically related inlet-ray bundles, said bundles being on axes defining an inlet plane, a second housing having a ray-outlet side and adapted to mount binocular viewing elements on spaced parallel axes defining an outlet plane, said housings being pivotally interconnected on an axis parallel to the geometrical intersection of said inlet and outlet planes, the range of pivotal relative movement of said housings being less than 180°, and a single plane-surface mirror contained within at least one of said housings at the region of their pivotal connection of said housings and including mechanical tilt-stabilizing and angle-dividing connections to both housings, said mirror being of such effective area proportions as to accept incidence of both inlet-ray bundles within said first housing and to reflect said bundles alike within said second housing regardless of the instantaneous angular pivoted relation between said housings, said second housing including optical means accepting both reflected ray bundles and transmitting the same with equal path length and in spaced relation for binocular viewing on the respective axes of said outlet side; like binocular-viewing elements mounted to said second housing, each binocular-viewing element comprising an axis-offsetting arm mounted to said second housing for adjustable rotation about one of said spaced parallel axes of the outlet plane, like folding mirrors on each of the spaced parallel axes of the outlet plane, said mirrors being adjustably mounted to permit precision parallel alignment of said axes for said binocular viewing elements, and a single control member carried by said second housing and connected to said axis-offsetting arms for counter-rotating adjustment actuation thereof.

2. As an article of manufacture, a binocular viewing head for a stereoscopic microscope, said head comprising a first housing having a ray-inlet side adapted to be mounted to a microscope body and adapted to accommodate two laterally spaced stereoscopically related inlet-ray bundles, said bundles being an axes defining an inlet plane, a second housing having a ray-outlet side and adapted to mount binocular viewing elements on spaced parallel axes defining an outlet plane, said housings being pivotally interconnected on an axis parallel to the geometrical intersection of said inlet and outlet planes, the range of pivotal relative movement of said housings being less than 180°, and a single plane-surface mirror contained within at at least one of said housings at the region of their pivotal connection of said housings and including mechanical tilt-stabilizing and angle-dividing connections to both housings, said mirror being of such effective area proportions as to accept incidence of both inlet-ray bundles within said first housing and to reflect said bundles alike within said second housing regardless of the instantaneous angular pivoted relation between said housings, said second housing including optical means accepting both reflected ray bundles and transmitting the same with equal path length and in spaced relation for binocular viewing on the respective axes of said outlet side; like binocular-viewing elements mounted to said second housing, each binocular-viewing element comprising an axis-offsetting arm mounted to said second housing for adjustable rotation about one of said spaced parallel axes of the outlet plane, and a single control member carried by said second housing and connected to said axis-offsetting arms for counter-rotating adjustment actuation thereof.

* * * * *